(12) United States Patent
Williamson et al.

(10) Patent No.: US 6,273,133 B1
(45) Date of Patent: Aug. 14, 2001

(54) FLUID FLOW RATE SWITCHING DEVICE

(75) Inventors: Mark E. Williamson, Wonder Lake; Scott Ariagno, Mundelein, both of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/418,650

(22) Filed: Oct. 15, 1999

(51) Int. Cl.⁷ .................................................... F16K 11/08
(52) U.S. Cl. ................................. 137/625.32; 137/625.3
(58) Field of Search ........................... 137/625.3, 625.32; 251/118

(56) References Cited

U.S. PATENT DOCUMENTS

| | | | |
|---|---|---|---|
| 3,276,472 | 10/1966 | Jinkens et al. | 137/556 |
| 3,678,960 | 7/1972 | Leibinsohn | 137/625.47 |
| 3,774,604 | 11/1973 | Danielsson | 128/214.4 |
| 3,834,372 | 9/1974 | Turney | 128/2 F |
| 4,210,178 * | 7/1980 | Morse et al. | 137/625.5 |
| 4,375,813 | 3/1983 | Hessel | 128/214 |
| 4,566,480 | 1/1986 | Parham | 137/271 |
| 4,593,717 | 6/1986 | Levasseur | 137/556.6 |
| 4,694,856 | 9/1987 | Leibinsohn | 137/555 |
| 4,738,283 * | 4/1988 | Shirai et al. | 137/625.32 |
| 4,967,797 | 11/1990 | Manska | 137/625.47 |
| 5,009,251 * | 4/1991 | Pike et al. | 137/561 A |
| 5,427,145 | 6/1995 | Grabenkort | 137/616.7 |
| 5,439,452 | 8/1995 | McCarty | 604/248 |
| 5,443,453 | 8/1995 | Walker et al. | 604/248 |
| 5,466,228 | 11/1995 | Evans | 604/248 |
| 5,499,968 | 3/1996 | Milijasevic et al. | 604/30 |
| 5,817,068 | 10/1998 | Urrutia | 604/248 |

FOREIGN PATENT DOCUMENTS

| | | |
|---|---|---|
| 44 19 369 A1 | 12/1994 | (DE) . |
| 195 48 537 A1 | 7/1996 | (DE) . |
| 0 800 837 A2 | 10/1997 | (EP) . |

OTHER PUBLICATIONS

Translation of Cols. 9–10 of DE 44 19 369 A1.
Translation of Col. 3 of DE 195 48 537 A1.

* cited by examiner

Primary Examiner—John Fox
(74) Attorney, Agent, or Firm—Jeffrey C. Nichols; Mark J. Buonaiuto; Francis C. Kowalik

(57) ABSTRACT

A fluid flow rate switching device providing a plurality of precise user selectable flow rates. Generally, the device includes a housing having a port and a plurality of passages. Respectively disposed in each of the passages is a rigid capillary tube for regulating the flow rate of a therapeutic fluid through the passages. Further, a valve is rotatably connected to the housing for operably connecting and disconnecting the port from one or more of the passages.

83 Claims, 5 Drawing Sheets

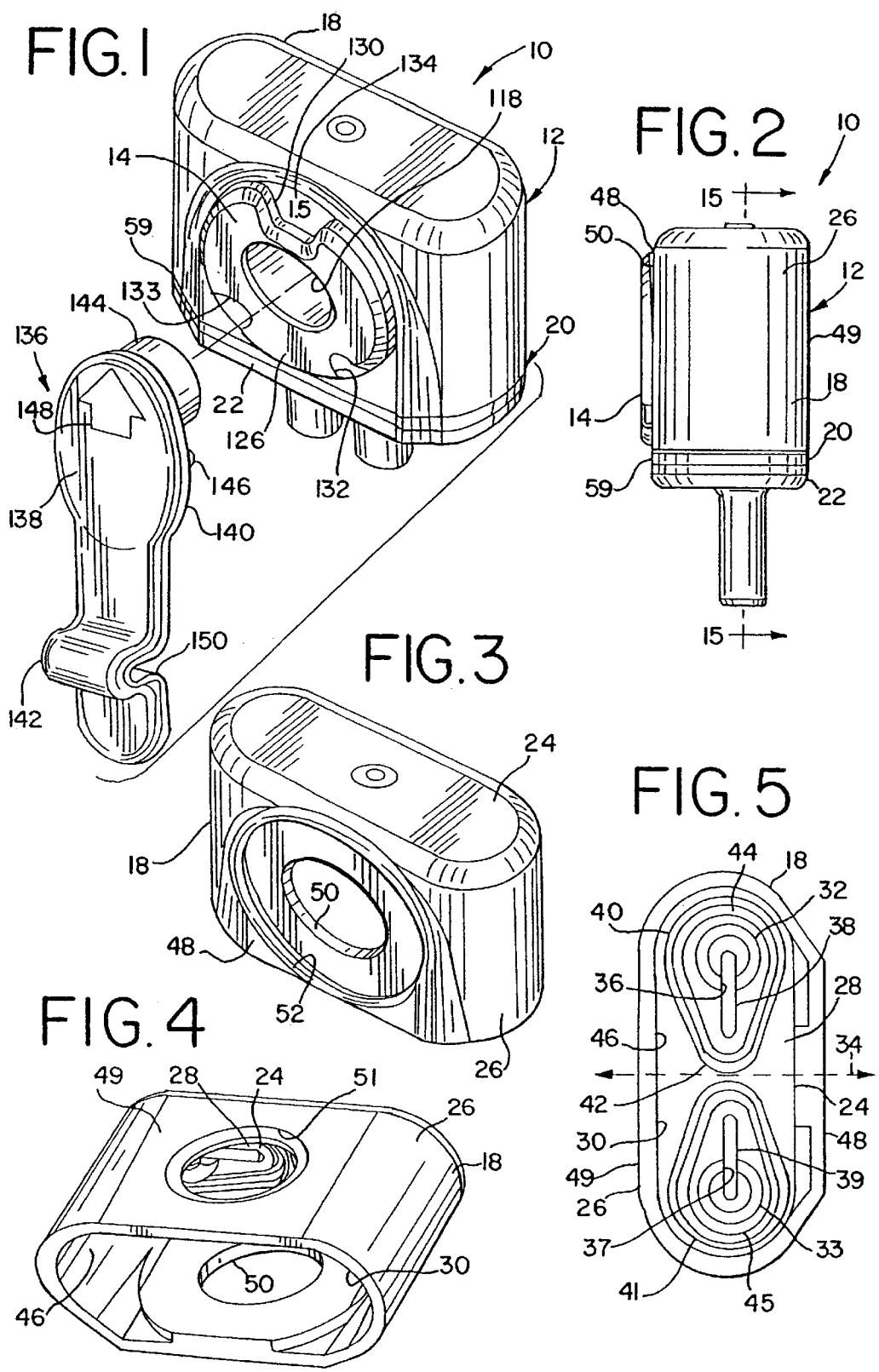

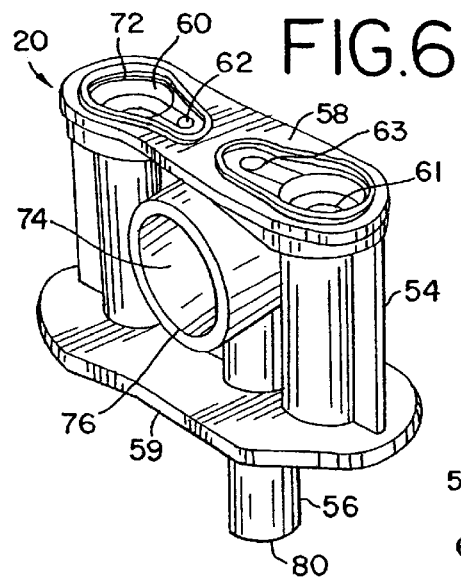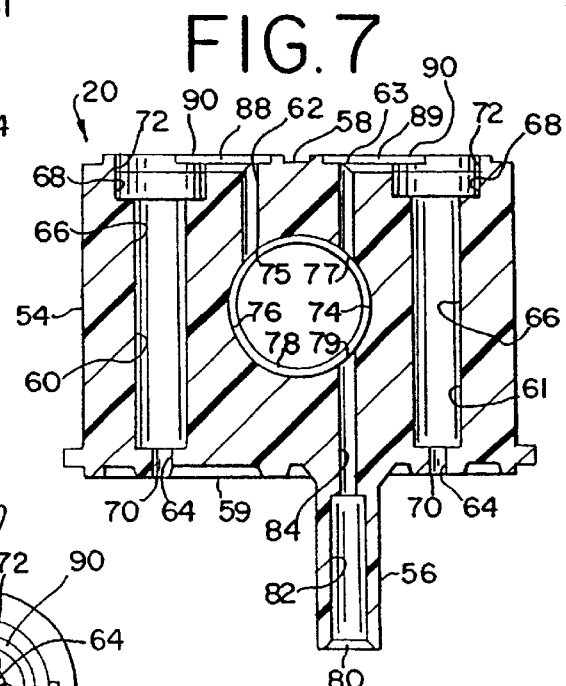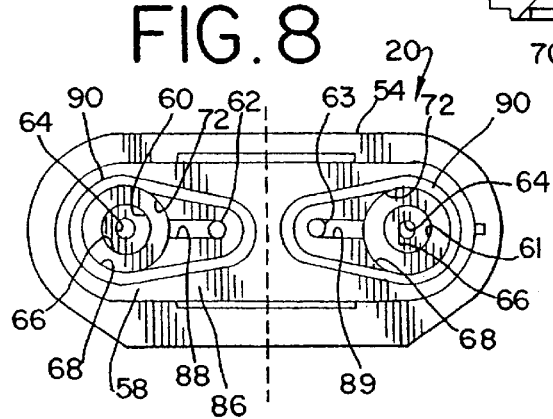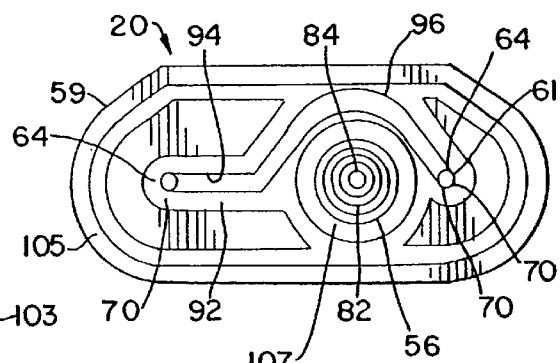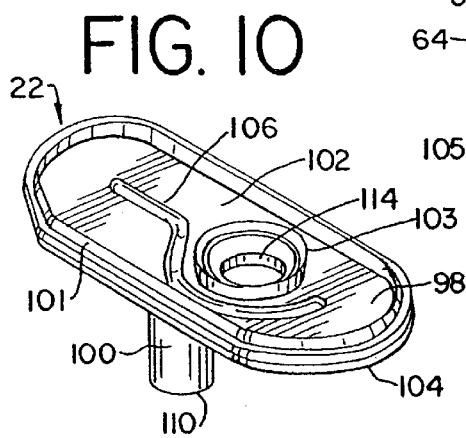

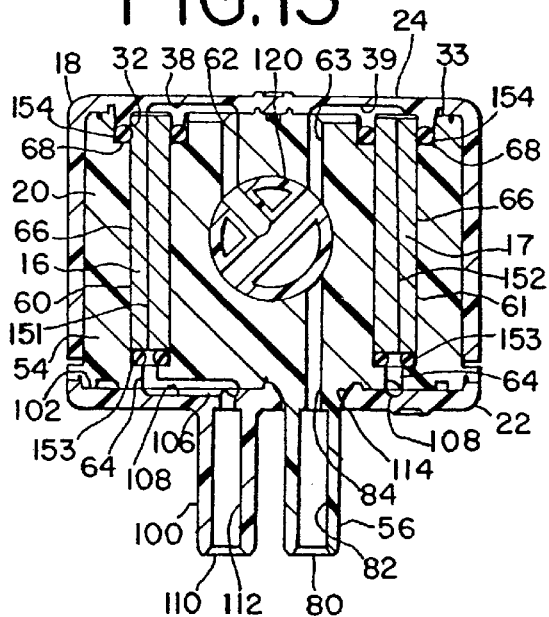
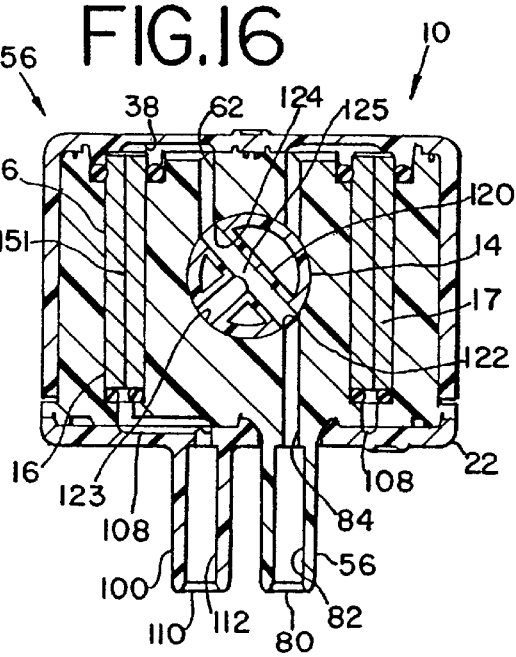
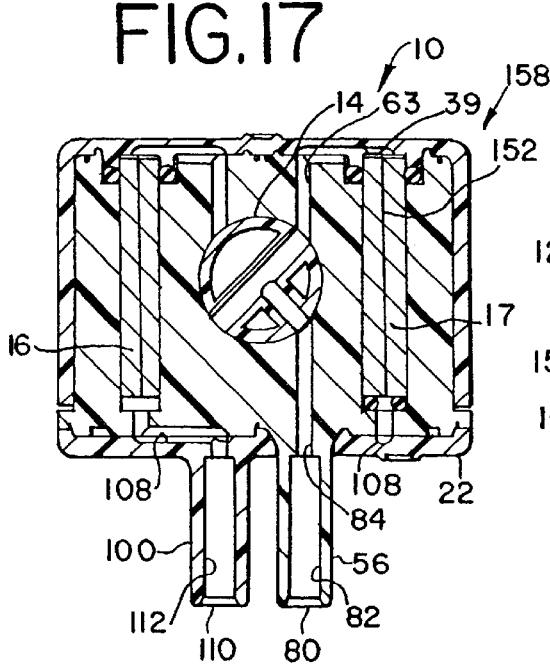
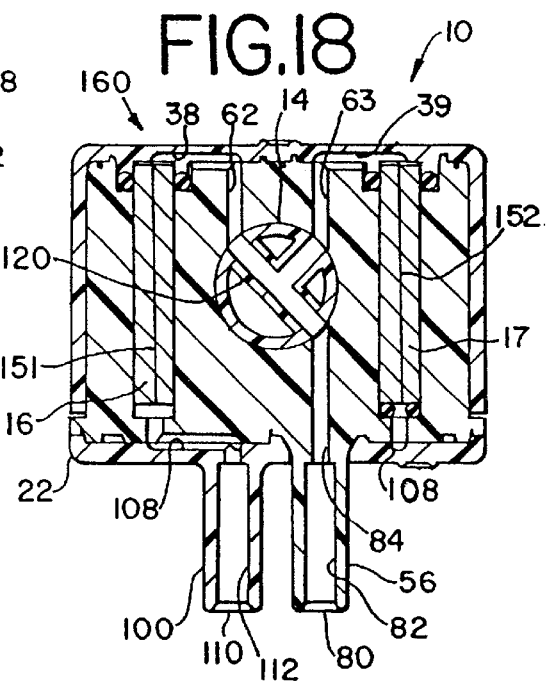

FLUID FLOW RATE SWITCHING DEVICE

DESCRIPTION

1. Technical Field

The present invention generally relates to devices for controlling flow rates of fluids, and in particular to providing a plurality of precise user selectable flow rates in medical fluid delivery systems.

2. Background Art

In many fluid delivery systems, it is important to carefully control the fluid flow rates. With respect to systems intended to be used in the intravenous administration of fluids, the precise control of fluid flow rates is usually a critical part of the therapy being provided to the patient. In the medical field, then, accuracy is an important feature of a flow control system. Furthermore, the intravenous administration of fluids at uncontrolled high fluid flow rates can be harmful to the patient.

Another desirable feature of a flow control system is consistency over time. In the medical field, it is impractical to expect a medical attendant to be present to monitor the fluid flow rate during the entire treatment session. A flow rate control system must therefore be capable of maintaining a stable flow rate while being unattended for relatively long periods of time. Also in the medical field, as well as other environments, yet another desirable feature for a flow control system is simplicity of operation to minimize operator error.

In some drug administration systems, a valve is used in combination with a pair of plastic flexible tubes to create a fluid rate switching device. However, the use of plastic flexible tubing fails to provide high accuracy in regulating the flow rate of a fluid, Also, the length of plastic tubing required to achieve a desired flow rate can change as a result of inconsistencies in the manufacturing process of plastic tubing. Thus, special steps must be taken if plastic tubing is to be used in regulating a fluid flow rate.

Hence, prior to the present invention, a need existed for a relatively small device having a user selectable flow rate control that is precise and stable.

SUMMARY OF THE INVENTION

Generally, the switch of the present invention includes a housing having a port and a plurality of passages. Respectively disposed in each of the passages is a rigid capillary tube for regulating the flow rate of a therapeutic fluid through the passages. Further, a valve is rotatably connected to the housing for operably connecting and disconnecting the port from one or more of the passages.

Other advantages and features of the present invention will be apparent from the following description of a specific embodiment illustrated in the accompanying drawings.

BRIEF DESCRIPTION OF DRAWINGS

FIG. 1 is an enlarged perspective assembly view of a switching device and a removable handle in accordance with the present invention with the switching device having a housing and a switching valve, the housing including a cover, an insert, and an end cap;

FIG. 2 is a side view of the switching device of FIG. 1;

FIG. 3 is a top perspective view of the cover to the housing depicted in FIG. 1;

FIG. 4 is a bottom perspective view of the cover to the housing depicted in FIG. 1;

FIG. 5 is an elevated view of the inner surface of the end wall to the housing cover depicted in FIGS. 3 and 4;

FIG. 6 is a perspective view of the insert to the housing depicted in FIG. 1;

FIG. 7 is a cross-sectional view of the insert depicted in FIG. 6;

FIG. 8 is a top view of the insert depicted in FIG. 6;

FIG. 9 is a bottom view of the insert depicted in FIG. 6;

FIG. 10 is a perspective view of the end cap to the housing depicted in FIG. 1;

FIG. 15 is a cross-sectional view of the switching device taken along plane 15—15 of FIG. 2 and with the valve turned to the off position;

FIG. 16 is similar to FIG. 15, except with the valve turned to enable a single serial flow path through the switching device;

FIG. 17 is similar to FIG. 16, except with the valve turned to enable an alternative single serial flow path through the switching device;

FIG. 18 is similar to FIGS. 16 and 17, except with the valve turned to enable a dual parallel flow path through the switching device;

DETAILED DESCRIPTION

Figure 11:
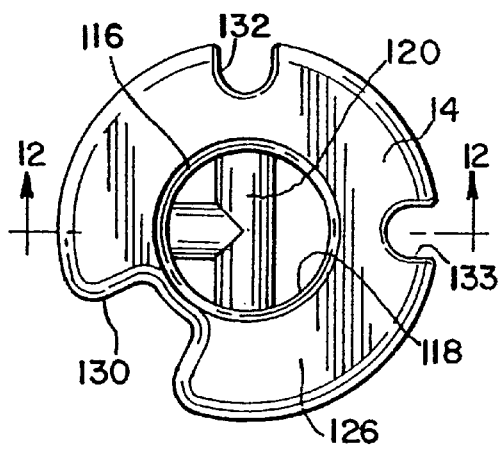
FIG. 11 is an enlarged top view of the valve within the switching device depicted in FIG. 1.

While this invention is susceptible of embodiments in many different forms, there is shown in the drawings and will herein be described in detail a preferred embodiment of the invention. The present disclosure is to be considered as an exemplification of the principles of the invention and is not intended to limit the broad aspect of the invention to the embodiment illustrated.

Referring now to the drawings, and particularly to FIGS. 1 and 2, a multi rate switching device 10 is disclosed having a housing 12, a valve 14, and a pair of flow restrictors 16, 17 (FIGS. 15–18). The housing 12 includes an outer cover member 18, an insert 20, and an end cap 22. These components are preferably made of polycarbonate and attached together by ultrasonic welding. However, if desired, the components can be fabricated from other rigid polymeric materials such as cyclic olefin containing polymers, bridged polycyclic hydrocarbon containing polymers, polyesters, polyamides, ABS, polyurethane and the like and can be attached together by adhesive bonding, solvent bonding, radio frequency bonding, snapfits, or other suitable joining methods.

Turning to FIGS. 3, 4 and 5, the outer cover 18 includes an end wall 24 and a continuous perimeter wall 26 integrally connected together. The end wall 24 has an inner surface 28 (FIGS. 4 and 5) and a generally oval shaped perimeter. The perimeter wall 26 extends from the perimeter of the end wall 24 and defines an opening 30 for receiving the insert 20.

As shown in FIG. 5, a pair of C-shaped projections 32, 33 are integrally attached and extend from the inner surface 28 of the cover member end wall 24. The C-shaped projections 32,33 are symmetrically positioned about the lateral axis 34 of the end wall 24. Preferably, the C-shaped projections 32 and 33 have openings 36 and 37, respectively, that face each other.

Extending through each opening 36,37 of the C-shaped projections 32 and 33 is a longitudinal channel 38 and 39, respectively. The channels 38,39 are formed in the surface 28 of the end wall 24 and are symmetrically positioned about the end wall lateral axis 34. Each channel 38 and 39 originates generally at the midpoint of its associated C-shaped projection 32 and 33, respectively, and extends along the longitudinal axis of the end wall 24. The channels 38,39 terminate short of reaching the lateral axis 34 of the end wall 24.

Extending from and integrally attached to the inner surface 28 of the end wall 24 are a pair of continuous walls 40, 41 that surround each C-shaped projection 32, 33 and associated channel 38,39. The continuous walls 40,41 are symmetrically positioned about the lateral axis 34 of the end wall 24 with each wall having a generally teardrop shaped perimeter. The walls 40,41 facilitate attaching the cover 18 to the insert 20 to define two separate fluid paths as described in detail further herein. Preferably, the apex 42 of the teardrop shaped perimeters of the two walls 40,41 face each other. Bordering the inner perimeter of each wall 40 and 41 is a continuous groove 44 and 45, respectively, formed within the inner surface 28 of the end wall 24.

As previously indicated, extending from the perimeter of the outer cover end wall 24 is a continuous perimeter wall 26 that is generally oval in cross section and defines an open chamber 46 for receiving the housing insert 20. The perimeter wall 26 includes opposing outer side surfaces 48,49 with coaxially aligned annular apertures 50 and 51 passing through the side surfaces 48 and 49, respectively. Outer side surface 48 also includes a ring shaped outer ridge 52 in coaxial alignment with aperture 50. Preferably, outer side surface 49 is generally planar to enhance comfort when placing the side surface against the skin of a patient. Likewise, the portions of the perimeter wall 26 between side surfaces 48 and 49 are smooth.

Turning to FIGS. 6–9, the insert 20 of the housing 12 includes a flow block 54 and a tube member 56 integrally attached together. The flow block 54 includes an inner plate member 58 and an outer plate member 59. Preferably, the plate members 58,59 are in coplanar spaced relationship to each other.

As shown in FIG. 7, formed within the flow block 54 and extending through the inner plate member 58 and the outer plate member 59 are a pair of stepped outer bores 60,61 and a pair of inner bores 62,63. The outer bores 60,61 are in parallel spaced relationship to each other and perpendicular to the plate members 58,59. Each outer bore 60,61 includes a cylindrical passage 64, a cylindrical restrictor containment chamber 66, and a cylindrical o-ring containment chamber 68. The cylindrical passage 64 of each outer bore 60,61 is in fluid communication with containment chamber 66 and has an opening 70 in the outer plate member 59. The containment chamber 66 of each bore 60,61 is in fluid communication with the o-ring containment chamber 68 and has an inner diameter that is larger than the inner diameter of the cylindrical passage 64. The o-ring chamber 68 of each bore 60,61 has an opening 72 in the inner plate member 58 and a larger inner diameter than the inner diameter of the restrictor containment chamber 66.

The inner bores 62,63 within the flow block 54 are in parallel spaced relationship to each other and the outer bores 60,61. Also, the inner bores 62,63 are situated between the outer bores 60,61. The inner bores 62,63 extend through the inner plate member 58 and to the inner surface 74 of a cylindrical control valve receiving bore 76 situated between the inner plate member 58 and the outer plate member 59. Accordingly, the inner bores 62 and 63 are in fluid communication with ports 75 and 77, respectively, on the inner surface 74 of valve receiving bore 76.

Preferably, the longitudinal axis of the control valve receiving bore 76 is in spaced perpendicular relationship to the longitudinal axises of the outer bores 60,61 and the inner bores 62,63. Moreover, a retaining ring 78 radially inwardly projects about one opening of the control valve receiving bore 76.

Tube member 56 of the housing insert 20 has a distal port or opening 80 and a cylindrical bore 82 in coaxial alignment and fluid communication with a junction bore 84 extending into the flow block 54. The junction bore 84 also is in longitudinal coaxial alignment with inner bore 63 and in fluid communication with the control valve receiving bore 76 via port 79.

As shown in FIG. 8, formed in the outer surface 86 of the housing insert inner plate member 58 are a pair of longitudinal channels 88,89 symmetrically positioned about the lateral axis of the plate member. Each channel 88,89 is in fluid communication and extends between one of the o-ring chambers 68 and one of the inner bores 62,63 in the flow block 54. When the cover member 18 is attached to the insert 20, channels 38 (FIG. 5) and 88 define a generally cylindrical passage within the housing 12 along with channels 39 (FIG. 5) and 89.

A pair of continuous walls 90 surround the channel 88,89, o-ring bore opening 72 and inner bore opening on both sides of the inner plate member 58 about the lateral axis. The walls 90 are integrally attached and perpendicularly extend from the surface 86 of the inner plate member 58. The walls 90 are dimensioned to correspond, align, and at least be partially received with the continuous grooves 44,45 formed within the inner surface 28 of the housing outer cover end wall 24. This results in a tortuous path, or flashtrap,for preventing debris particles from being deposited within the device fluid paths during ultrasonic welding of the walls 40,41 of the housing end wall 24 to the inner plate member 58 of the housing insert 20.

As shown in FIG. 9, the outer plate member 59 of the flow block 54 includes an outer surface 92 having a channel 94 in fluid communication and extending between the outer bores 64. The channel 94 includes a curved portion 96 wherein the channel extends around tube member 56.

Referring to FIG. 10, the end cap 22 of the housing 12 includes a plate like cover member 98 and a tube member 100 integrally attached together. The cover member 98 attaches to the outer plate member 59 on the housing insert 20. The cover member 98 includes an inner surface 102 and an opposite outer surface 104. The inner surface 102 includes a channel 106 that is symmetrical to the channel 94 formed in the outer surface 92 of the flow block outer plate member 59. Accordingly, with the end cap 22 attached to the flow block 54, the two channels 106 and 94 define a single tubular fluid passageway 108 (FIGS. 15–18) between the outer bores 60 and 61.

Preferably, the inner surface 102 of the cover member 98 includes a outer perimeter weld ring 101 and an inner weld ring 103 about an aperture 114. The weld rings 101 and 102 are received within corresponding channels 105 and 107 (FIG. 9), respectively, formed in the outer surface 92 of the housing insert outer plate member 59. Thus, during ultrasonic welding of the rings 101,102 of the cover member 98 to the outer plate member 59, a flashtrap similar to that used in attaching the housing cover 18 to the housing insert 20 is provided for preventing debris particles from entering the fluid paths of the device.

Turning to FIG. 15, the tube member 100 of the end cap 22 includes a cylindrical bore 112 extending through cover member 98 and having a distal port or opening 110. The bore 112 is in fluid communication with the channel 106 in the inner surface 102 of the cover member 98, and thus passageway 108.

The cover member 98 of the end cap 22 also includes aperture 114 for receiving the tube member 56 extending from the flow block 54 of the housing insert 20. Accordingly, the housing insert tube member 56 extends through the aperture 114 when the cover member 98 is attached to the housing insert 20.

Figure 12:
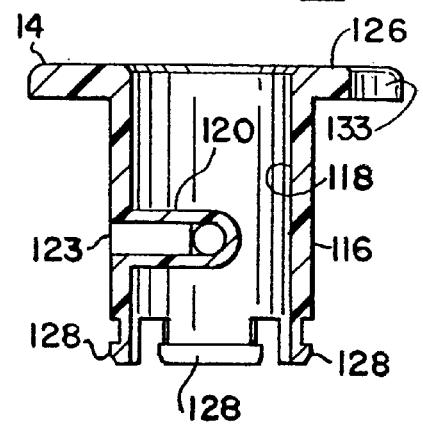
FIG. 12 is a cross-sectional view of the valve of FIG. 11 taken along plane 12—12.

Referring to FIGS. 1, 11 and 12, the valve 14 of the switching device 10 includes a cylindrical hub member 116 rotatably mounted within the valve receiving bore 76 (FIG. 7) of the insert member 20 and the apertures 50,51 (FIGS. 3 and 4) of the housing outer cover member 18. Preferably, the valve 14 consists of high-density polyethylene. Also, a lubricant or grease such as a high viscosity silicon oil is used to seal and reduce friction between the valve hub 116 and housing insert member bore 76.

As shown in FIGS. 11 and 12, the hub 116 includes a bore 118 containing a tubular fluid path connecting joint or T-joint fitting 120 integrally attached to the hub. Turning to FIG. 16, the outer surface of the hub member 116 includes three valve ports 122,123 and 124 in fluid communication with the T-joint fitting 120. Preferably, relative to the center junction 125 of the T-joint fitting 120, port 122 is situated ninety degrees from port 123 and one hundred eighty degrees from port 124.

Turning back to FIGS. 11 and 12, radially outwardly extending from one end of the hub member 116 is a flange member 126 partially received within the ring shaped outer ridge 52 (FIGS. 1–3) of the switching device 10. The recessing of the flange 126 into the housing 12 is intended to prevent a patient from tampering with the device by attempting to manually rotate the valve 14.

Formed in the outer perimeter of the flange member 126 is a flow rate indicator window or notch 130 and a pair of handle engagement notches 132,133. The indicator window 130 allows a user to view a rate label 134 (FIG. 1) printed on the housing 12 and corresponding to a user selected flow rate. Accordingly, the valve flange member hides all other rate labels except for the currently selected rate. As the user rotates the valve 14 to change the rate, the window 130 rotates and exposes only the selected rate. Alternatively, instead of exposing the selected rate label through a window in the valve flange, a pointer could be used to identify the selected rate.

Preferably, relative to the longitudinal axis of the hub member 116, the center of the indicator window 130 is between valve ports 122 and 123 (FIG. 16). Further, engagement notches 132 and 133 are centered about one hundred and thirty five degrees from both sides of the indicator window 130.

As shown in FIG. 12, longitudinally extending from the valve hub member 16 opposite the flange 126 are a group of prongs 128. Both the flange member 126 and the prongs 128 are integrally attached to the hub member 116. The distal ends of the prongs 128 are radially outwardly lipped. The prongs 128 secure the valve 14 to the housing 12 by engaging the retaining ring 78 (FIG. 7) within the control valve receiving bore 76. However, the valve 14 is allowed to rotate within the control valve receiving bore 78 for selecting a flow rate as described in detail further herein.

Figure 13:
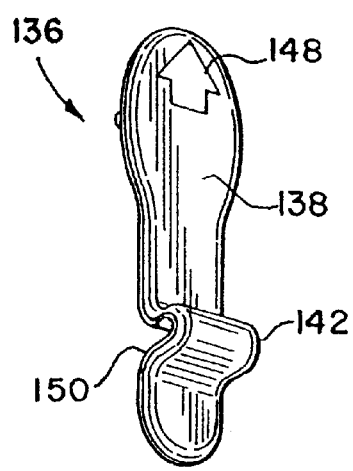
FIG. 13 is a top perspective view of the rate switching tool or handle of FIG. 1 for removably attaching to the valve of FIG. 11.
Figure 14:
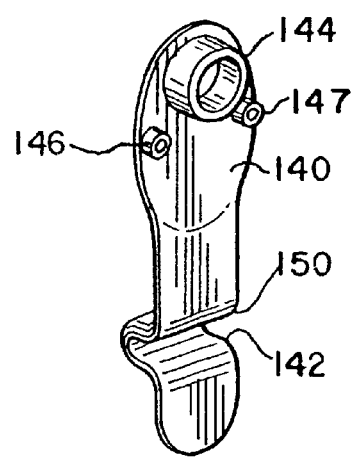
FIG. 14 is a bottom perspective view of the handle depicted in FIG. 13.

Turning to FIGS. 1, 13 and 14, manually attachable to the valve 14 is a rate switching tool or handle 136 for providing leverage to manually rotate the valve. As explained in detail further herein, rotation of the valve 14 results in a selection of a flow rate path through the switch 10. Preferably, the handle 136 is needed to rotate the valve 14. Accordingly, the handle 136 can be removed and kept by a physician or other health care personnel to discourage patients from rotating the valve without permission.

Figure 19:
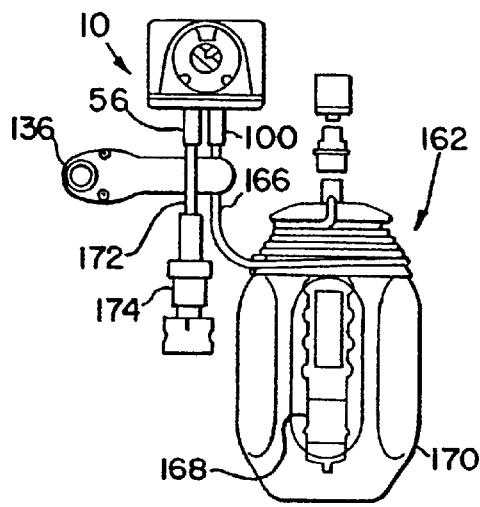
FIG. 19 is an elevated view of the switching device of FIG. 1 operably coupled to a small volume elastomeric infusion pump.
Figure 20:
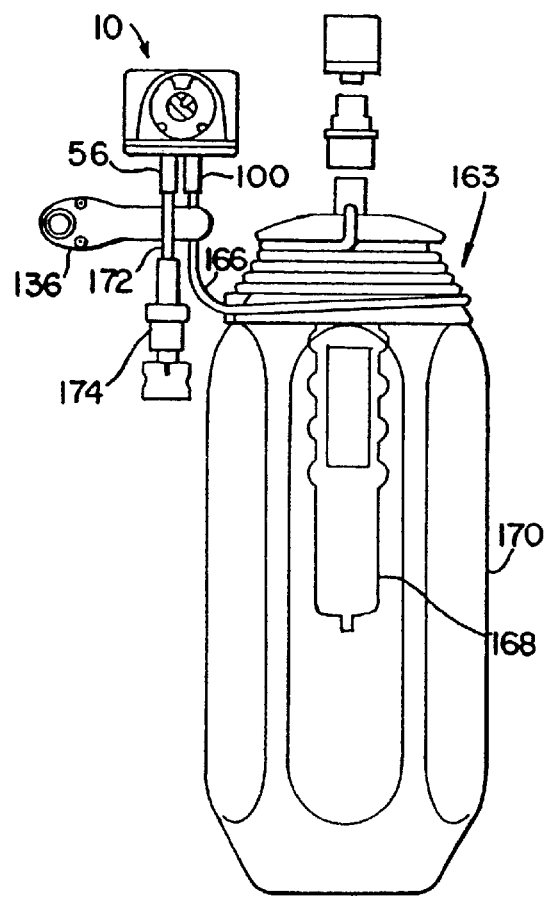
FIG. 20 is an elevated view of the switching device of FIG. 1 operably coupled to a large volume elastomeric infusion pump; and, FIG. 21 is an elevated view of the switching device of FIG. 1 operably coupled to an infusor.
Figure 21:
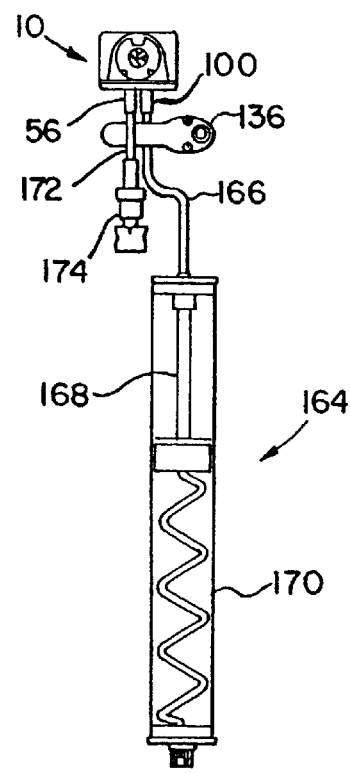

The handle 136 includes an indicator side 138, an opposite valve engagement side 140, and a tube attachment crook 142. The engagement side 140 of the handle 136 includes a cylindrical registration hub 144 receivable within the bore 118 of the valve hub 116 about flange 126. The engagement side 140 of the handle 136 also includes a pair of spaced coupling pins 146 and 147 that are received within the notches 132 and 133, respectively, when the handle is attached to the valve 14. Moreover, the indicator side 138 of the handle can include indicia 148 for pointing to the valve window 130 when the handle is attached to the valve 14. Further, the crook 142 in the handle 142 defines an opening 150 for receiving, and thus clipping, the handle to tubing or the like as shown in FIGS. 19–21.

Turning to FIG. 15, and referring to the housing insert 20, received within the containment chamber 66 of each outer bore 60 and 61 is a capillary tube or restrictor 16 and 17, respectively. Each restrictor 16 and 17 has a calibrated longitudinal axial open bore 151 and 152, respectively, for regulating the flow rate of a fluid. Preferably, the restrictors 16,17 have substantially the same length and consist of microbored glass tubes with restrictor 17 allowing for twice the flow rate of restrictor 16. However, in alternative embodiments, restrictor 17 can have another flow rate other than twice that of restrictor 16.

Preferably, the restrictors 16,17 are located on opposite sides of the valve 14 rather than being in-line with each other to reduce the overall length of the device. However, if desired, the restrictors 16,17 can be mounted in other configurations with respect to each other.

Also located within the containment chamber 66 of each outer bore 60,61 is a spacer o-ring 153 proximate to each passage 64 within the flow block 54. The o-rings 153 provide an adjustable cushion to account for tolerance stackup and remove air space between the molded housing insert 20 and the restrictors 16,17.

Received within the o-ring containment chamber 68 of each outer bore 60 and 61 is a sealing o-ring 154. The o-rings 154 are attached to the outer surfaces of the restrictors 16,17 to form liquid tight seals. Further, the C-shaped projections 32,33 of the housing cover member 18 compress the o-rings 154 against the flow block 54 proximate to the containment chambers 66. Thus, liquid tight seals are provided between the inner walls of each o-ring containment chamber 68 and the o-rings 154. Nevertheless, a flow path is provided between outer bore 16 and inner bore 62 via channel 38 in the end wall 24 of the housing outer cover member 18. Likewise, a flow path is provided between outer bore 17 and inner bore 63 via channel 39 in the end wall 24 of the housing outer cover member 18.

As shown in FIGS. 15–18, rotation of the valve 14 results in turning off or selecting a flow path between the ports 80,110 of the rate switching device 10 that correspond to a desired fluid flow rate. Manual rotation of the valve 14 to the position shown in FIG. 15 results in the valve blocking, and thus turning off, all flow paths between the ports 80,110 of the rate switching device 10.

Manual rotation of the valve 14 to the position shown in FIG. 16 results in a single serial flow path 156 between the ports 80,110 of the rate switching device 10. The flow path 156 extends from port 110 to port 80 via tube member bore 112, passageway 108, bore 151 of restrictor 16, channel 38, inner bore 62, T-joint 120, flow block bore 84, and tube member bore 82.

Manual rotation of the valve 14 to the position shown in FIG. 17 results in another single serial flow path 158 between the ports 80,110 of the rate switching device 10. The flow path 158 extends from port 110 to port 80 via tube member bore 112, passageway 108, bore 152 of restrictor 17, channel 39, inner bore 63, T-joint 120, flow block bore 84, and tube member bore 82.

Manual rotation of the valve 14 to the position shown in FIG. 18 results in a parallel flow path 160 between the ports 80,110 of the rate switching device 10. The parallel flow path 160 consists both flow path 156 and 158. Accordingly, fluid flows from port 110 to port 80 via tube member bore 112, passageway 108, bore 152 of restrictor 17, channel 39, inner bore 63, T-joint 120, flow block bore 84, and tube member bore 82. Fluid also flows from port 110 to port 80 via tube member bore 112, passageway 108, bore 151 of restrictor 16, channel 38, inner bore 62, T-joint 120, flow block bore 84, and tube member bore 82.

As shown in FIGS. 15–18, the T-joint fitting 120 of the valve 14 intercepts the bores 62,63,84 of the flow block 20 at an offset or angle of about 135 degrees when making a fluid flow connection. This Y-configuration greatly reduces the size of the device 10 wherein, the smaller the device, the more comfortable it is for a patient to wear, and the Y-configuration also provides for adjustments of the fluid flow rate in a logical incremental ascending or descending order. For instance, if the restrictor 16 in flow path 156 provides a 1ml/hour flow rate, and the restrictor 17 in flow path 158 provides a 2 ml/hour flow rate, then the resulting rates that can be selected using device 10 are, in order, 1 ml/hour (FIG. 16), 2 ml/hour (FIG. 17), 3 ml/hour (FIG. 18), and 0 ml/hour (FIG. 15).

Preferably, the flow paths and corresponding flow rates through the device 10 are selected when the valve 14 is rotated by an predetermined incremental amount. For instance, as shown in FIG. 15–18. Rotating the valve 10 ninety (90) degrees results in turning off the device 10 or the selection of a flow path and corresponding flow rate through the device 10.

In particular, counterclockwise rotation of the valve ninety degrees from the position shown in FIG. 15 results in the selection of the flow path and corresponding flow rate through the device 10 shown in FIG. 16. Likewise, counterclockwise rotation of the valve ninety degrees from the position shown in FIG. 16 results in the selection of the flow path and corresponding flow rate through the device 10 shown in FIG. 17. Further, counterclockwise rotation of the valve ninety degrees from the position shown in FIG. 17 results in the selection of the flow path and corresponding flow rate through the device 10 shown in FIG. 18. Preferably, the flow rate through the device 10 incrementally increases as the valve 14 is rotated with the handle 136 in a counterclockwise direction. Likewise, flow rate through the device 10 incrementally decreases as the valve 14 is rotated with the handle 136 in a clockwise direction. Thus, the device 10 operates in a logical manner similar to regulating the flow rate of liquid with most faucets by turning the faucet handle clockwise to decrease the flow rate of the liquid and turning the facet handle counterclockwise to increase the flow rate of the liquid.

In an embodiment depicted in FIGS. 19, 20, and 21, the switching device 10 can be operably connected to various positive pressure sources including, among others, elastomeric infusion pumps 162,163, and 164, respectively, via flexible tubing 166. Such pumps are well know in the art and can include that disclosed in U.S. Pat. No. 5,263,935 to Hessel, incorporated herein by reference. Preferably, the restrictors 16,17 within the switching device are matched to the amount of fluid pressure produced by a pressure source for providing the desired flow rates through the device.

Pumps 162,163, and 164 include an elastomeric bladder 168 disposed with a generally tubular outer casing 170. The bladder 168 can be filled with a pharmaceutically active material. The fluid pressure within the fully extended bladder results in the fluid flow from the pump to the switching device via tubing 166. Preferably, the tubing 166 is connected by solvent bonding to tube 100 of the switching device 10 so fluid flows from the pump, through the restrictors 16,17, and then through the valve 14. Further, tube 56 is attached by solvent bonding to flexible tubing 172 having a connector 174 attached opposite the switching device 10. The connector 174 provides for operably connecting the switching device 10 to I.V. tubing or the like attached to the patient.

As will be appreciated by those having skill in the art, the switching device 10 can also be operably connected to other types of positive pressure sources including electromechanical, chemical, and gravitational.

While the specific embodiments have been illustrated and described, numerous modifications come to mind without significantly departing from the spirit of the invention and the scope of protection is only limited by the scope of the accompanying Claims.

What is claimed is:

1. A switch for selecting a flow rate of a therapeutic fluid comprising:

a housing having a port and a plurality of passages;

a plurality of rigid capillary tubes that regulate the flow rate of the therapeutic fluid, each of the tubes respectively disposed in one of the passages; and, a valve operably connected to the housing, the valve moveable to selectively connect and disconnect the port from one or more of the passages and having a flange attached to a hub member, the flange having an outer perimeter and said housing having an aperture and an annular ridge in coaxial alignment with the aperture, the aperture receiving the hub of the valve and the ridge surrounding a substantial portion of the flange outer perimeter.

2. The switch of claim 1 wherein the flow rate of the therapeutic fluid is sequentially increased by at least three incremental valves as the valve is rotated in a counterclockwise direction.

3. The switch of claim 1 wherein the flow rate of the therapeutic fluid is incrementally increased as the valve is sequentially rotated in at least three serial steps of ninety degrees.

4. The switch of claim 1 wherein the flow rate of the therapeutic fluid is sequentially decreased by at least three incremental values as the valve is rotated in a clockwise direction.

5. The switch of claim 1 wherein said valve is moveable to a serial flow position to operably connect one of the passages to the port, the valve moveable to a parallel flow position to operably connect at least two of the passages to the port, and the valve moveable to an off position to operably disconnect the port from the passages.

6. The switch of claim 1 wherein said housing includes a cover member ultrasonically welded to an insert containing the capillary tubes, and the cover member and the insert defining a flashtrap to prevent debris particles from coming into contact with the therapeutic fluid.

7. The switch of claim 1 wherein said housing includes a bore that receives the valve.

8. The switch of claim 1 wherein said flange includes a window to reveal flow rate information through the switch.

9. The switch of claim 1 wherein the valve includes a fluid path.

10. The switch of claim 9 wherein the fluid path of the valve operably connects to a pair of parallel spaced fluid passages within the housing.

11. The switch of claim 10 wherein the fluid path of the valve angularly connects to the spaced fluid passages within the housing.

12. The switch of claim 10 wherein the fluid path of the valve connects to at least one of the spaced fluid passages within the housing at an angle of one hundred and thirty five degrees.

13. The switch of claim 10 wherein the fluid path of the valve is T-shaped.

14. The switch of claim 1 wherein the valve is removably attachable to a handle.

15. The switch of claim 14 wherein the handle includes a crook adapted to receive a portion of a tube.

16. The switch of claim 1 wherein the capillary tubes are microbored glass.

17. The switch of claim 1 wherein the capillary tubes allow different flow rates of the therapeutic fluid.

18. A method of selecting a flow rate of a therapeutic fluid with the switch of claim 1 comprising the steps of:
providing a pump means containing the therapeutic fluid;
providing the switch of claim 1 operably connected to the pump means;
moving the valve to a serial flow position that operably connects one of the passages to the pump means; and
moving the valve to a parallel flow position that operably connects at least two of the passages to the pump means.

19. The method of claim 18 further comprising the step of incrementally increasing the flow rate through the switch as the valve is rotated.

20. A switch for selecting a flow rate of a therapeutic fluid comprising:
a housing having a port and a plurality of passages;
a plurality of rigid capillary tubes that regulate the flow rate of the therapeutic fluid, each of the tubes respectively disposed in one of the passages; and,
a valve operably connected to the housing, the valve having a fluid flow path and movable to selectively connect and disconnect the port from one or more of the passages.

21. The switch of claim 20 wherein the flow rate of the therapeutic fluid is sequentially increased by at least three incremental values as the valve is rotated in a counterclockwise direction.

22. The switch of claim 20 wherein the flow rate of the therapeutic fluid is incrementally increased as the valve is sequentially rotated in at least three serial steps of ninety degrees.

23. The switch of claim 20 wherein the flow rate of the therapeutic fluid is sequentially decreased by at least three incremental values as the valve is rotated in a clockwise direction.

24. The switch of claim 20 wherein said valve is moveable to a serial flow position to operably connect one of the passages to the port, the valve moveable to a parallel flow position to operably connect at least two of the passages to the port, and the valve moveable to an off position to operably disconnect the port from the passages.

25. The switch of claim 20 wherein said housing includes a cover member ultrasonically welded to an insert containing the capillary tubes, and the cover member and the insert defining a flashtrap to prevent debris particles from coming into contact with the therapeutic fluid.

26. The switch of claim 20 wherein said housing includes a bore that receives the valve.

27. The switch of claim 20 wherein said valve includes a flange attached to a hub member.

28. The switch of claim 27 wherein said flange includes a window to reveal flow rate information through the switch.

29. The switch of claim 27 wherein said flange has an outer perimeter and said housing includes an aperture and an annular ridge in coaxial alignment with the aperture, the aperture receiving the hub of the valve and the ridge surrounding a substantial portion of the flange outer perimeter.

30. The switch of claim 20 wherein the fluid path of the valve operably connects to a pair of parallel spaced fluid passages within the housing.

31. The switch of claim 30 wherein the fluid path of the valve angularly connects to the spaced fluid passages within the housing.

32. The switch of claim 30 wherein the fluid path of the valve connects to at least one of the spaced fluid passages within the housing at an angle of one hundred and thirty five degrees.

33. The switch of claim 30 wherein the fluid path of the valve is T-shaped.

34. The switch of claim 20 wherein the valve is removably attachable to a handle.

35. The switch of claim 34 wherein the handle includes a crook adapted to receive a portion of a tube.

36. The switch of claim 20 wherein the capillary tubes are microbored glass.

37. The switch of claim 20 wherein the capillary tubes allow different flow rates of the therapeutic fluid.

38. A method of selecting a flow rate of a therapeutic fluid with the switch of claim 20 comprising the steps of:
providing a pump means containing the therapeutic fluid;
providing the switch of claim 20 operably connected to the pump means;
moving the valve to a serial flow position that operably connects one of the passages to the pump means; and,
moving the valve to a parallel flow position that operably connects at least two of the passages to the pump means.

39. The method of claim 38 further comprising the step of incrementally increasing the flow rate through the switch as the valve is rotated.

40. An infusor system for providing a flow rate of a therapeutic fluid to a patient comprising:
a housing and a valve operably connected together, the housing containing a plurality of rigid restrictors that regulate the flow rate of the therapeutic fluid through the housing and the valve being moveable to selectively pass the therapeutic fluid through the restrictors, and the valve including a flange having a window to reveal flow rate information.

41. The system of claim 40 wherein the flow rate of the therapeutic fluid is sequentially increased by at least three incremental values as the valve is rotated.

42. The system of claim 40 wherein the flow rate of the therapeutic fluid is incrementally decreased as the valve is sequentially rotated in at least three serial steps of ninety degrees.

43. The system of claim 40 wherein said valve is moveable to a serial flow position to allow the therapeutic fluid to pass through only one of the restrictors and the valve moveable to a parallel flow position to allow the therapeutic fluid to pass through at least two of the restrictors.

44. The system of claim 40 wherein the valve includes a fluid path that operably connects to a pair of parallel spaced fluid passages within the housing.

45. The system of claim 40 wherein the fluid path angularly connects to the spaced fluid passages within the housing.

46. The system of claim 40 wherein a handle is removably attachable to the valve.

47. The system of claim 46 wherein the handle includes a crook adapted to receive a portion of a tube.

48. The system of claim 40 wherein the restrictors are microbored glass tubes.

49. The system of claim 40 wherein the restrictors allow different flow rates of the therapeutic fluid.

50. The system of claim 40 wherein a pump means for containing the therapeutic fluid is operably connected to the housing.

51. The system of claim 50 wherein the valve allows a user to operably connect one of the restrictors to the pump means.

52. The system of claim 51 wherein the valve allows the user to operably connect at least two of the restrictors to the pump means.

53. The system of claim 51 wherein the valve allows the user to incrementally increase the flow rate through the housing as the valve is rotated.

54. The system of claim 40 wherein said housing includes a cover member ultrasonically welded to an insert containing the restrictors, and the cover member and the insert defining a flashtrap to prevent debris from coming into contact with the therapeutic fluid.

55. An infusor system for providing a flow rate of a therapeutic fluid to a patient comprising:
a housing and a valve operably connected together, the housing containing a plurality of rigid restrictors that regulate the flow rate of the therapeutic fluid through the housing, the valve being moveable to selectively pass the therapeutic fluid through the restrictors, and a handle removably attachable to the valve, the handle having a crook adapted to receive a portion of a tube.

56. The system of claim 55 wherein the flow rate of the therapeutic fluid is sequentially increased by at least three incremental values as the valve is rotated.

57. The system of claim 55 wherein the flow rate of the therapeutic fluid is incrementally decreased as the valve is sequentially rotated in at least three serial steps of ninety degrees.

58. The system of claim 55 wherein said valve is moveable to a serial flow position to allow the therapeutic fluid to pass through only one of the restrictors and the valve moveable to a parallel flow position to allow the therapeutic fluid to pass through at least two of the restrictors.

59. The system of claim 55 wherein said valve includes a flange having a window to reveal flow rate information.

60. The system of claim 55 wherein the valve includes a fluid path that operably connects to a pair of parallel spaced fluid passages within the housing.

61. The system of claim 60 wherein the fluid path angularly connects to the spaced fluid passages within the housing.

62. The system of claim 55 wherein the restrictors are microbored glass tubes.

63. The system of claim 55 wherein the restrictors allow different flow rates of the therapeutic fluid.

64. The system of claim 55 wherein a pump means for containing the therapeutic fluid is operably connected to the housing.

65. The system of claim 64 wherein the valve allows a user to operably connect one of the restrictors to the pump means.

66. The system of claim 65 wherein the valve allows the user to operably connect at least two of the restrictors to the pump means.

67. The system of claim 66 wherein the valve allows the user to incrementally increase the flow rate through the housing as the valve is rotated.

68. The system of claim 55 wherein said housing includes a cover member ultrasonically welded to an insert containing the restrictors, and the cover member and the insert defining a flashtrap to prevent debris from coming into contact with the therapeutic fluid.

69. An infusor system for providing a flow rate of a therapeutic fluid to a patient comprising:
a housing and a valve operably connected together, the housing containing a plurality of rigid restrictors that regulate the flow rate of the therapeutic fluid through the housing and the valve being moveable to selectively pass the therapeutic fluid through the restrictors, said housing including a cover member ultrasonically welded to an insert containing the restrictors, and the cover member and the insert defining a flashtrap to prevent debris from coming into contact with the therapeutic fluid.

70. The system of claim 69 wherein the flow rate of the therapeutic fluid is sequentially increased by at least three incremental values as the valve is rotated.

71. The system of claim 69 wherein the flow rate of the therapeutic fluid is incrementally decreased as the valve is sequentially rotated in at least three serial steps of ninety degrees.

72. The system of claim 69 wherein said valve is moveable to a serial flow position to allow the therapeutic fluid to pass through only one of the restrictors and the valve moveable to a parallel flow position to allow the therapeutic fluid to pass through at least two of the restrictors.

73. The system of claim 69 wherein said valve includes a flange having a window to reveal flow rate information.

74. The system of claim 69 wherein the valve includes a fluid path that operably connects to a pair of parallel spaced fluid passages within the housing.

75. The system of claim 74 wherein the fluid path angularly connects to the spaced fluid passages within the housing.

76. The system of claim 69 wherein a handle is removably attachable to the valve.

77. The system of claim 76 wherein the handle includes a crook adapted to receive a portion of a tube.

78. The system of claim 69 wherein the restrictors are microbored glass tubes.

79. The system of claim 69 wherein the restrictors allow different flow rates of the therapeutic fluid.

80. The system of claim 69 wherein a pump means for containing the therapeutic fluid is operably connected to the housing.

81. The system of claim 80 wherein the valve allows a user to operably connect one of the restrictors to the pump means.

82. The system of claim 81 wherein the valve allows the user to operably connect at least two of the restrictors to the pump means.

83. The system of claim 82 wherein the valve allows the user to incrementally increase the flow rate through the housing as the valve is rotated.

* * * * *